US012678534B2

(12) United States Patent
Dorgan et al.

(10) Patent No.: US 12,678,534 B2
(45) Date of Patent: Jul. 14, 2026

(54) SUBMUCOSAL LIFTING AND HEMOSTATIC SEALING HYDROGEL

(71) Applicant: BOSTON SCIENTIFIC SCIMED, INC., Maple Grove, MN (US)

(72) Inventors: Philip David Dorgan, Cork (IE); Edward Joseph Devlin, Cork (IE); Conor O'Sullivan, Cork (IE); John Murphy, Cork (IE); Mark Looney, Cork (IE); Paul O'Farrell, Cork (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 456 days.

(21) Appl. No.: 18/311,205

(22) Filed: May 2, 2023

(65) Prior Publication Data

US 2023/0355834 A1     Nov. 9, 2023

Related U.S. Application Data

(60) Provisional application No. 63/337,726, filed on May 3, 2022.

(51) Int. Cl.
*A61L 24/08* (2006.01)
*A61L 24/00* (2006.01)

(52) U.S. Cl.
CPC .......... *A61L 24/08* (2013.01); *A61L 24/0015* (2013.01); *A61L 24/0031* (2013.01); *A61L 2300/418* (2013.01); *A61L 2400/04* (2013.01)

(58) Field of Classification Search
CPC .. A61L 24/08; A61L 24/0015; A61L 24/0031; A61L 2300/418; A61L 2400/04
See application file for complete search history.

(56) References Cited

U.S. PATENT DOCUMENTS

| | | | |
|---|---|---|---|
| 5,415,863 A | 5/1995 | Williams et al. | |
| 10,478,527 B2 | 11/2019 | Phillips et al. | |
| 10,751,444 B2 | 8/2020 | Pillay et al. | |
| 2017/0281862 A1 | 10/2017 | Raybin et al. | |
| 2018/0021252 A1 | 1/2018 | Delaney et al. | |
| 2019/0247301 A1 | 8/2019 | Hollyer et al. | |
| 2021/0322629 A1 | 10/2021 | Lydecker et al. | |

FOREIGN PATENT DOCUMENTS

| | | | |
|---|---|---|---|
| EP | 1466630 | * | 10/2004 |
| EP | 2783709 | * | 10/2014 |
| EP | 2783709 A1 | | 10/2014 |
| WO | 2013093164 A1 | | 6/2013 |
| WO | 2015099083 A1 | | 7/2015 |
| WO | 2020225336 A1 | | 11/2020 |
| WO | 2021212017 A1 | | 10/2021 |

OTHER PUBLICATIONS

Villegas-Peralta et al. Polymer Bulletin (2021) 78813-832).*
Biranje et al. (Review Paper) 28; 8899-8937 (2021)).*
Alven et al., "Chitosan and Cellulose-Based Hydrogels for Wound Management", International Journal of Molecular Sciences, 30 pages, 2020.
Kaspar et al., "Characterization of Spray Dried Chitosan-TPP Microparticles Formed by Two- and Three- Fluid Nozzles", Elsevier, 10 pages, 2013.
Pillai et al., "Injectable Nano Whitlockite Incorporated Chitosan Hydrogel for Effective Hemostasis", ACS Appl. Bio Mater, 2,2,865-873, 8 pages, 2019.
Yang et al., "Hydroxyapatite: A Promising Hemostatic Component in Orthopaedic Applications", Biology, Engineering and Medicine, 5 pages, 2017.
International Search Report and Written Opinion dated Sep. 7, 2023 for International Application No. PCT/US2023/020748.
Dong et al., "Enhanced Hemostatic Performance of Tranexamic Acid-Loaded Chitosan/Alginate Composite Microparticles," Journal of Biomedicine and Biotechnology, vol. 212, Article ID 981321, 9 pages, Oct. 1, 2012.
Tang et al., "Easily-Injectable Shear-Thinning Hydrogel Provides Long-Lasting Submucosal Barrier for Gastrointestinal Endoscopic Surgery," Bioactive Materials, vol. 15, pp. 44-52. Available Online Dec. 21, 2021.

* cited by examiner

*Primary Examiner* — Shirley V Gembeh
(74) *Attorney, Agent, or Firm* — Seager, Tufte & Wickhem LLP

(57) ABSTRACT

In some aspects, the present disclosure pertains to injectable polysaccharide-based hydrogels that comprises an anionic polysaccharide, a cationic crosslinking agent and a hemostatic agent. In some aspects, the present disclosure pertains to medical devices containing such injectable polysaccharide-based hydrogels, to kits that contain such injectable polysaccharide-based hydrogels, and to methods of using such injectable polysaccharide-based hydrogels.

20 Claims, 8 Drawing Sheets

SUBMUCOSAL LIFTING AND HEMOSTATIC SEALING HYDROGEL

CROSS REFERENCE TO RELATED APPLICATIONS

This application claims the benefit of U.S. Provisional Patent Application Ser. No. 63/337,726 filed on May 3, 2022, the disclosure of which is incorporated herein by reference.

TECHNICAL FIELD

The present disclosure relates to injectable gels that are useful for various medical procedures including use as lifting agents for endoscopic mucosal resection and dissection procedures.

BACKGROUND OF THE INVENTION

Injectable compositions are commonly used to separate one structure from another in order to separate, lift and/or stabilize the first structure for performing a medical diagnostic or treatment step safely, quickly and efficiently. For example, endoscopic procedures such as endoscopic mucosal resection (EMR), endoscopic submucosal dissection (ESD), colon polypectomy and peroroal endoscopic myotomy (POEM) are commonly performed to detect and remove malignant and pre-malignant lesions, tumors and/or otherwise unhealthy tissues within the mucosal and submucosal layers of the gastrointestinal (GI) tract. To reduce the risk of perforating the GI tract, healthcare providers commonly separate the submucosal layer from the underlying muscularis layer prior to performing the resection or dissection procedure. A typical way to establish this separation is to inject a fluid between the muscularis and submucosal tissue layers.

Surgical removal of the tissue creates an internal wound and is subject to hemorrhage. A common step in the procedure is to obtain adequate mucosal closure. Several techniques are available for mucosal closure including the use of endoscopic dips and/or endoscopic suturing.

SUMMARY

The present disclosure is directed to injectable hydrogel compositions that are useful in various medical procedures. The injectable hydrogel compositions are adapted to provide both submucosal lifting and hemostatic sealing treatment to the immediate tissue area after resection or dissection.

In some aspects, the present disclosure pertains to injectable polysaccharide-based hydrogels that comprise an anionic polysaccharide, a cationic crosslinking agent and a hemostatic agent.

In some embodiments, the anionic polysaccharide contains a repeating unit of glucuronic acid. In a particular example, the anionic polysaccharide comprises gellan gum.

In some embodiments, which can be used in conjunction with the preceding aspects and embodiments, the anionic polysaccharide is provided at a concentration ranging from about 0.010% to about 2.5%, with respect to the total weight of the injectable polysaccharide-based hydrogel.

In some embodiments, which can be used in conjunction with the preceding aspects and embodiments, the cationic crosslinking agent comprises a salt comprising a divalent metal cation and/or the crosslinking agent comprises a branched polyamine that comprises two or more primary amine groups that are positively charged at a pH of the hydrogel.

In some embodiments, which can be used in conjunction with the preceding aspects and embodiments, the cationic crosslinking agent is provided at a concentration ranging from about 0.005% to about 2.5%, with respect to the total weight of the injectable polysaccharide-based hydrogel.

In some embodiments, which can be used in conjunction with the preceding aspects and embodiments, the hemostatic agent is selected from an organic polymeric hemostatic agent, a small molecule organic hemostatic agent, a large molecule organic hemostatic agent, and an inorganic hemostatic agent. In specific embodiments, the hemostatic agent may be selected from chitosan, hydroxyapatite or tranexamic acid.

In some embodiments, which can be used in conjunction with the preceding aspects and embodiments, the hemostatic agent is in particulate form and is less than 50000 nm in average particle size.

In some embodiments, which can be used in conjunction with the preceding aspects and embodiments, the hemostatic agent is provided at a concentration ranging from about 5% to about 50%, with respect to the total weight of the injectable polysaccharide-based hydrogel.

In some embodiments, which can be used in conjunction with the preceding aspects and embodiments, the injectable polysaccharide-based hydrogel further comprises a coloring agent.

In some aspects, the present disclosure pertains to medical devices comprising a reservoir that contains an injectable polysaccharide-based hydrogel in accordance with any of the preceding aspects and embodiments.

In some embodiments, the reservoir is a syringe barrel.

In some embodiments, the medical device comprises a needle through which the injectable polysaccharide-based hydrogel is injected.

In some aspects, the present disclosure pertains to the use of a medical device in accordance with any of the above aspects and embodiments in a medical procedure in which an upper mucosal layer is elevated from a lower layer.

In some aspects, the present disclosure pertains to a method of separating and elevating an upper mucosal layer from a lower layer, the method comprising injecting an injectable polysaccharide-based hydrogel in accordance with any of the preceding aspects and embodiments through a needle into a target treatment site between the upper mucosal layer and the lower layer.

In some embodiments, the method further comprises removing tissue raised by the injectable polysaccharide-based hydrogel.

In some embodiments, the method is performed as part of an endoscopic mucosal resection procedure or an endoscopic submucosal dissection procedure.

In some embodiments, the method is performed using a medical device that further comprises a flexible tube that couples a syringe barrel to the needle, and the injectable polysaccharide-based hydrogel is injected from the syringe barrel, through the flexible tube, through the needle and into the target site.

In some aspects, the present disclosure pertains to kits that comprise a medical device in accordance with any of the preceding aspects and embodiments and one or more items selected from (a) an endoscopic injection needle, (b) a tissue resection device, (c) a tissue retrieval device, and (d) an endoscope, within a suitable packaging material.

DETAILED DESCRIPTION

Figure 1A:
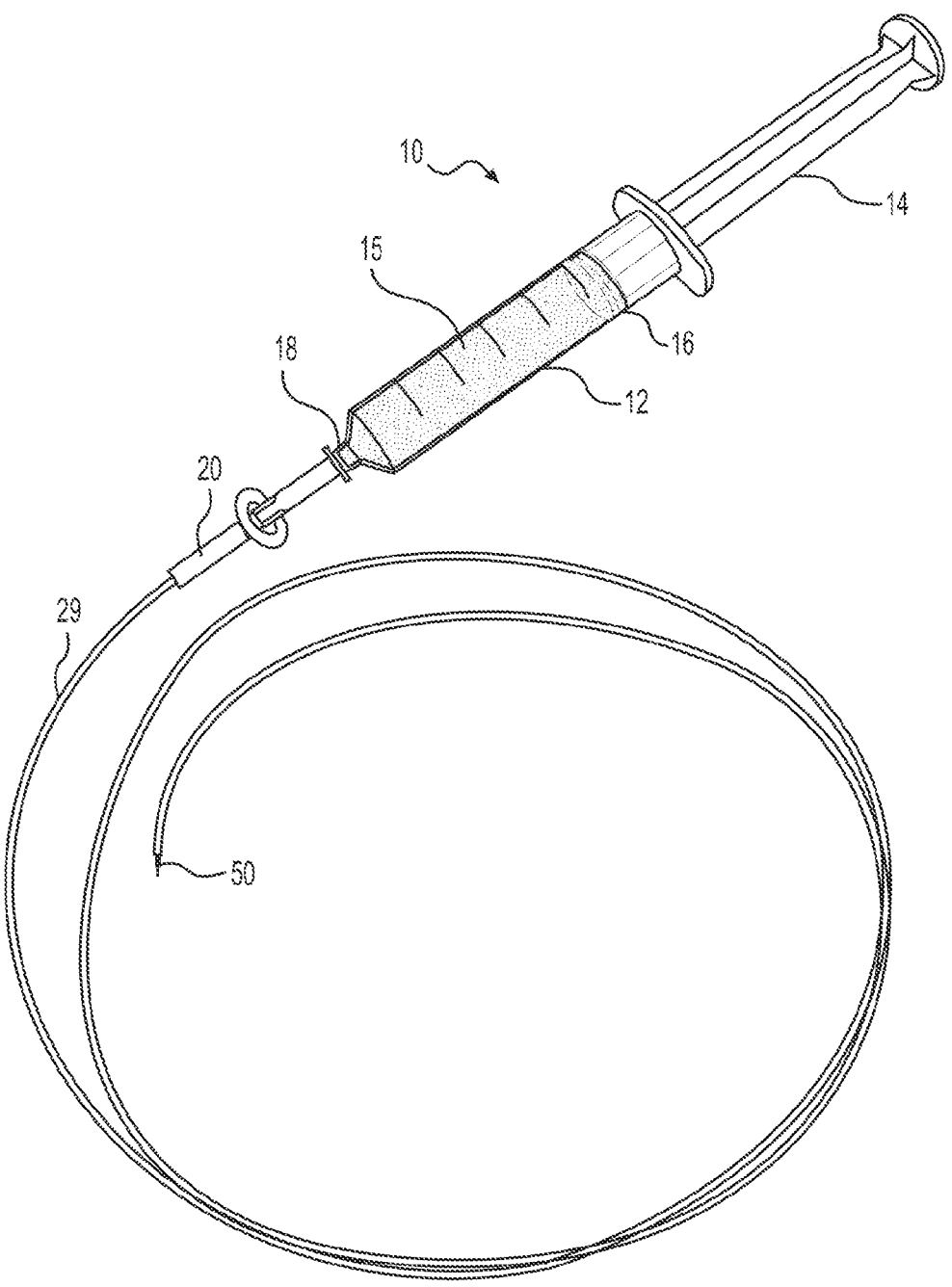
FIGS. 1A-1C show exemplary medical devices in accordance with certain aspects of the present disclosure.

The present disclosure pertains to polysaccharide-based hydrogels that contain a hemostatic reagent at the point of administration. The hydrogels allow the tissue to lift, facilitating surgical removal. The hydrogels also have hemostatic properties to reduce or prevent hemorrhage at the surgical site. In this way, the need for intervention using dips or sutures may be eliminated. Moreover, the hydrogels may reduce the incidence of interoperable bleeds from the surrounding tissue, which can occur post-procedure upon dipping or suturing removal.

According to various aspects of the present disclosure, the polysaccharide-based hydrogels may comprise a polysaccharide, a crosslinking agent and a hemostatic agent at the point of administration. In some embodiments, the polysaccharide, the crosslinking agent and the hemostatic agent are provided in a single injectable composition. In some embodiments, the polysaccharide is crosslinked to form a hydrogel within a reservoir and is injected into the patient as a hydrogel from the reservoir.

In some embodiments, a first injectable composition comprising the polysaccharide and the crosslinking agent is co-administered with a second injectable composition comprising the hemostatic agent.

A number of options are available for administering the polysaccharide, crosslinking agent, and hemostatic agent to a target site in a patient including the following, among others: (a) particles of the hemostatic agent may be suspended in a hydrogel that comprises the polysaccharide and the crosslinking agent, (b) the hemostatic agent may be dissolved in a hydrogel that comprises the polysaccharide and the crosslinking agent, (c) an injectable composition comprising the hemostatic agent in which particles of the hemostatic agent is suspended in a liquid or a hydrogel may be co-administered with an injectable hydrogel composition comprising the polysaccharide and the crosslinking agent, (d) an injectable composition comprising the hemostatic agent dissolved in a liquid or hydrogel may be co-administered with an injectable hydrogel composition comprising the polysaccharide and the crosslinking agent, or (e) the hemostatic agent may be in a dry state (e.g., as pure particles, coated particles, etc.) and premixed with a hydrogel composition comprising the polysaccharide and the crosslinking agent before administration.

Suitable polysaccharides for use in forming the injectable compositions of the present disclosure include natural polysaccharides (e.g., natural gums such as vegetable gums and/or microbial gums) and synthetic polysaccharides. The polysaccharides in the compositions of the present disclosure are typically anionic polysaccharides. Non-limiting examples of the polysaccharides include anionic polysaccharides that contain a repeating unit of glucuronic add, such as gellan gum, alginate, and xanthan gum, among others.

In various embodiments, gellan gum may be preferred. As used herein, "gellan gum" refers to a polysaccharide (e.g., produced by Sphingomnas bacteria), and has a general structure formed of repeating units of four sugars linked together: two residues of D-glucose, one residue of L-rhamnose, and one residue of D-glucuronic acid. The polysaccharide may comprise one or more types of gellan gum, e.g., native gellan gum, deacylated gellan gum, or a mixture thereof. Native gellan gum may include two acyl groups (e.g., acetate and glycerate), bound to the glucose residue adjacent to the glucuronic acid residue. These acyl groups may be removed under alkaline conditions to produce deacylated gellan gum, which results in different stability and plasticity properties in comparison to native gellan gum. For example, native gellan gum generally forms softer, more elastic gels with thermoreversibility, whereas deacylated gellan gum generally forms harder, more inelastic gels with higher heat resistance. In at least one embodiment, the injectable composition comprises deacylated gellan gum. Additional information regarding polysaccharide hydrogels can be found, for example, in U.S. Patent Application Pub. Nos. 2019/0247301, 2018/0021252 and 2017/0281862, the disclosures of which are hereby incorporated by reference.

Certain microbial extracts may comprise endotoxins, e.g., lipopolysaccharides from the bacteria that become combined with the polysaccharide structure. In some embodiments, the polysaccharide(s) may be chosen to minimize or eliminate the introduction of endotoxins into the composition. In some examples, the polysaccharide(s) may have an endotoxin level of 20 endotoxin units (EU) or less. Bacterial endotoxin levels may be measured, for example, using the Limulus Amebocyte Lysate (LAL) test. Alternatively, or additionally, the polysaccharide(s) may be processed to reduce or eliminate the concentration of endotoxins prior to use in the composition disclosed herein. For example, the composition may comprise a microbial-sourced polysaccharide that has been processed to reduce the amount of endotoxins present, such that the resulting composition is pharmaceutically-acceptable and in compliance with the applicable government regulatory standards In some embodiments, the polysaccharide is provided at a concentration ranging from about 0.01% or less to about 2.5% or more, with respect to the total weight of the polysaccharide-based hydrogel at the point of administration. For example, the polysaccharide may be provided at a concentration ranging anywhere from about 0.010% to about 0.025% to about 0.05% to about 0.10% to about 0.25% to about 0.5% to about 0.75% to about 1.0% to about 1.25% to about 1.5% to about 1.75% to about 2.0% to about 2.25% to about 2.5% (in other words, ranging between any two or the preceding numerical values), with respect to the total weight of the polysaccharide-based hydrogel at the point of administration.

Suitable crosslinking agents for use in forming the polysaccharide-based hydrogels of the present disclosure include covalent crosslinking agents and/or ionic crosslinking agents. The crosslinking agents in the injectable compositions of the present disclosure more typically comprise multivalent cationic crosslinking agents. In particularly beneficial embodiments, the injectable compositions may comprise a salt comprising a divalent cation. Non-limiting examples of such salts include salts comprising divalent metal cations such as calcium and/or magnesium cations, e.g., calcium chloride ($CaCl_2$), magnesium sulfate ($MgSO_4$), magnesium chloride ($MgCl_2$), any hydrates thereof, and any mixture thereof. In one particular example, the salt(s) with a divalent cation comprise calcium chloride or a hydrate thereof, such as calcium chloride dihydrate. In some embodiments, the crosslinking agents may comprise a branched polyamine that comprises two or more primary amine groups that are positively charged at a pH of the hydrogel, wherein the branched polyamine ionically crosslinks the polysaccharide. Non-limiting examples of such branched polyamines include trilysine, tetralysine, pentalysine, tris(aminoalkyl)amines (e.g., tris(2-aminoethyl)amine, tris(aminoalkyl)alkanes (e.g., 1,1,1-tris(aminomethyl)ethane), and any mixture thereof.

In some cases, the polysaccharide-based hydrogels may comprise at least one salt comprising a monovalent cation and at least one salt comprising a divalent cation. For example, the injectable composition may comprise at least one sodium salt or potassium salt and at least one calcium or magnesium salt, such as, for example, Naa and $CaCl_2$, or Na and $MgCl_2$, or KCl and $CaCl_2$, or KC and $MgCl_2$, and so forth. Further, for example, the injectable compositions may comprise at least one monovalent salt chosen from sodium chloride, potassium chloride, sodium dihydrogen phosphate, potassium hydrogen phosphate, sodium gluconate, or sodium acetate trihydrate in combination with at least one salt chosen from calcium chloride, magnesium sulfate, or magnesium chloride.

In some embodiments, the salt with the divalent cation is provided at a concentration ranging from about 0.005% or less to about 0.200% or more, with respect to the total weight of the polysaccharide-based hydrogel at the point of administration. For example, the salt with the divalent cation may be provided at a concentration ranging anywhere from about 0.005% to about 0.010% to about 0.015% to about 0.020% to about 0.025% to about 0.030% to about 0.040% to about 0.050% to about 0.075% to about 0.100% to about 0.150% to about 0.200%, with respect to the total weight of the polysaccharide-based hydrogel at the point of administration.

In some embodiments, the salt with the monovalent cation is provided at a concentration ranging from about 0.1% or less to about 5.0% or more, with respect to the total weight of the polysaccharide-based hydrogel at the point of administration. For example, the salt with the monovalent cation may be provided at a concentration ranging anywhere from about 0.10% to about 0.25% to about 0.50% to about 0.75% to about 1.0% to about 1.5% to about 2.0% to about 5.0%, with respect to the total weight of the polysaccharide-based hydrogel at the point of administration.

Further, for example, the composition may comprise a salt solution having an osmolality ranging from about 240 mOsmol/kg to about 340 mOsmol/kg (e.g., 290 mOsmol/kg±50 mOsmol/kg), such as from about 250 mOsmol/kg to about 320 mOsmol/kg, or from about 280 mOsmol/kg to about 300 mOsmol/kg. The solution may be physiologically compatible, e.g., having electrolyte levels, osmolality, and pH suitable for injection into a patient. The pH of the solution may be adjusted using a suitable base such as sodium hydroxide to increase pH and/or a suitable acid such as hydrochloric acid, or may adjusted by other means or with other substances providing for a biocompatible composition.

As previously indicated, in addition to a polysaccharide and a crosslinking agent, the polysaccharide-based hydrogels of the present disclosure comprise a hemostatic agent at the point of administration.

Any suitable hemostatic agent may be employed in the present disclosure. Hemostatic agents for use in the present disclosure include organic polymeric hemostatic agents, small molecule hemostatic agents, inorganic hemostatic agents or large molecule hemostatic agents.

Organic polymeric hemostatic agents include those that comprise chitosan, chitosan derivatives, dextran and dextran derivatives.

Chitosan is a modified polysaccharide containing randomly distributed β-(1→4)-linked D-glucosamine (deacetylated unit) and N-acetyl-D-glucosamine (acetylated unit). Chitosan is produced commercially by the alkaline N-deacetylation of chitin, which is a cellulose-like polymer consisting primarily of unbranched chains of modified glucose, specifically N-acetyl-D-glucosamine The degree of deacetylation in commercial chitosans generally ranges from 60 to 70 to 80 to 90 to 100% although essentially any degree of deacetylation is possible. Commercial chitosan is available in a range of molecular weights, including low molecular weight chitosan (e.g., having a molecular weight ranging from 10 kDa to 190 kDa), medium molecular weight chitosan (e.g., having a molecular weight ranging from 190 kDa to 310 kDa), high molecular weight chitosan (e.g., having a molecular weight ranging from 310 kDa to 375 kDa) and ultra-high molecular weight chitosan (e.g., having a molecular weight above 375 kDa).

Chitosan is also positively charged in acidic to neutral solutions with a charge density dependent on the pH and the degree of deacetylation. The pka value of chitosan generally ranges from 6.1 to 7.0, depending on the degree of deacetylation. Thus, while substantially insoluble in distilled water, chitosan is generally soluble in dilute aqueous acid (e.g., pH=6.5 or less).

In some embodiments the chitosan is in organic salt form, including organic acid salts of chitosan based on acetic acid (acetate salt) or citric acid (citrate salt).

In some embodiments, the organic polymeric hemostatic agents comprise chitosan in soluble form.

In some embodiments, the organic polymeric hemostatic agents comprise chitosan in particulate form. In some embodiments, organic polymeric hemostatic agents in particulate form are freeze-dried.

In some embodiments, the particulate hemostatic agent comprises a core comprising a chitosan salt and a shell comprising a polyanionic crosslinking agent, for example, a polyphosphate crosslinking agents including lithium, sodium or potassium salts of tripolyphosphate, polymetaphosphates such as trimetaphosphate and hexametaphosphate. Particles have an inverse structure (i.e., having a core comprising tripolyphosphate and a shell comprising a chitosan salt) have been made. See Ondřej Kašpar et al., "Characterization of spray dried chitosan-TPP microparticles formed by two- and three-fluid nozzles," Powder Technology 240 (2013) 31-40. However, to the inventors' knowledge, core-shell particles having the structure of the present disclosure have not previously been prepared. Moreover, the particles in Kašpar et al. are directed to microencapsulation applications in which chitosan is used as an encapsulant.

In some embodiments, the organic polymeric hemostatic agent is provided at a concentration ranging from about 5% to about 50%, for example, ranging anywhere from 5% to 10% to 20% to 30% to 40% to 50%, with respect to the total weight of the polysaccharide-based hydrogel at the point of administration.

Where provided in particulate (insoluble) form, the organic polymeric hemostatic agent may have an average particle size, as measured by laser diffraction analysis or dynamic light scattering, ranging from 10 to 100,000 nm, for example, ranging anywhere from 10 nm to 25 nm to 50 nm to 100 nm to 250 nm to 500 nm to 750 nm to 1000 nm to 2,500 nm to 5,000 nm to 10,000 nm to 25,000 nm to 50,000 nm to 100,000 nm. In certain embodiments the average particle size ranges from 10 to 999 nm, for example, from 100 to 300 nm.

Where provided in particulate form, the organic polymeric hemostatic agent particles may comprise a shell that comprises a polyanionic crosslinking agent such as a polyanionic phosphate crosslinking agent.

Where provided in particulate form, the organic polymeric hemostatic agent particles may further be provided with a coating such as a thermosensitive coating or a pH sensitive coating.

Inorganic hemostatic agents include calcium phosphate minerals such as hydroxyapatite and Whitlockite. Hydroxyapatite which has the formula $Ca_5(PO_4)_3(OH)$, but is usually written as having the formula $Ca_{10}(PO_4)_6(OH)_2$. Whitlockite is reported to have the formula $Ca_9(MgFe)(PO_4)_6PO_3OH$.

In some embodiments, the inorganic hemostatic agent is provided at a concentration ranging from about 5% to about 50% for example, ranging anywhere from 5% to 10% to 20% to 30% to 40% to 50%, with respect to the total weight of the polysaccharide-based hydrogel at the point of administration.

The inorganic hemostatic agent may have an average particle size ranging from 10 nm to 999 nm, for example, ranging anywhere from 10 nm to 25 nm to 50 nm to 100 nm to 250 nm to 500 nm to 750 nm to 999 nm, typically 100 nm to 300 nm. Particles of the inorganic hemostatic agent may be provided with a coating such as a thermosensitive coating or a pH sensitive coating.

Small molecule organic hemostatic agents include amino acids such as tranexamic acid, aminocaproic add, and 4-aminomethylbenzoic acid.

In some embodiments, the small molecule organic hemostatic agent is provided at a concentration ranging from about 5% to about 50%, with respect to the total weight of the polysaccharide-based hydrogel at the point of administration.

The small molecule organic hemostatic agent may be provided in dissolved form or in particulate form, including soluble and insoluble particulate form. Where provided in particulate form, the small molecule organic hemostatic agent may have an average particle size ranging from 10 to 999 nm, for example, ranging anywhere from 10 nm to 25 nm to 50 nm to 100 nm to 250 nm to 500 nm to 750 nm to 999 nm, typically 100 to 300 nm.

Large molecule organic hemostatic agents include hemostatic proteins such as thrombin, fibrin and fibrinogen.

In some embodiments, the large molecule organic hemostatic agent is provided at a concentration ranging from about 5% to about 50% for example, ranging anywhere from 5% to 10% to 20% to 30% to 40% to 50%, with respect to the total weight of the polysaccharide-based hydrogel at the point of administration.

The large molecule organic hemostatic agent may be provided in dissolved form or in particulate form. Where provided in particulate form, the large molecule organic hemostatic agent may have an average particle size ranging from 10 to 999 nm, for example, ranging anywhere from 10 nm to 25 nm to 50 nm to 100 nm to 250 nm to 500 nm to 750 nm to 999 nm, typically 100 to 300 nm.

The compositions of the present disclosure may include further additives in addition to the polysaccharide, crosslinking agent and hemostatic agent described above.

In some embodiments, the compositions may comprise one or more coloring agents. In some cases, coloring agent (s) may allow for identification of the submucosal tissue plane upon injection into tissue, e.g., to determine the amount of tissue to be removed and/or assess the risk of perforation. Examples of the coloring agent(s) include, but are not limited to, brilliant blue (e.g., Brilliant Blue FCF, also known as FD&C Blue 1), indigo carmine (also known as FD&C Blue 2), indigo carmine lake, FD&C Blue 1 lake, methylene blue (also known as methylthioninium chloride), or a mixture thereof, among others.

In some embodiments, the compositions may comprise other suitable types of biocompatible agents. For example, the compositions may comprise agents to adjust the pH and/or tonicity of the compositions as appropriate. For example, the compositions may comprise one or more stabilizers and/or preservatives.

As previously indicated, the according to various aspects of the present disclosure, the compositions of the present disclosure may be used to create polysaccharide-based hydrogels that comprise a polysaccharide, a crosslinking agent and a hemostatic agent at a point of administration to a patient (e.g., at a target site between layers of tissue). Where the polysaccharide-based hydrogel is used as a submucosal lifting agent, after hydrogel injection and submucosal lifting, tissue resection and/or dissection may be performed. Surgical removal of the tissue creates an internal wound and is subject to hemorrhage. The hemostatic properties of the polysaccharide-based hydrogels promote hemostasis at administration site, for example, as a physical dotting agent, through elution the hemostatic agent (e.g., elution of a small molecule active pharmaceutical ingredient such as tranexamic add or aminocaproic acid), or both.

In some embodiments, the polysaccharide, the crosslinking agent and the hemostatic agent are provided in a single injectable composition. In some embodiments, a first injectable co-composition comprising the polysaccharide and the crosslinking agent is co-administered along with a second injectable co-composition comprising the hemostatic agent. Thus, in some embodiments, a crosslinked hydrogel is preloaded with a hemostatic agent and administered to a target site. In some embodiments, a crosslinked hydrogel is co-administered with a hemostatic agent.

As previously indicated, the hemostatic agent may be in solid form (e.g., as particles) or in solution form during administration. After administration, the hemostatic agent may change in form under physiological conditions. For example, particles of the hemostatic agent may dissolve under physiological conditions, or a solution of the hemostatic agent may precipitate under physiological conditions.

The hemostatic agent may provide immediate and/or extended treatment at the site of tissue-occlusion. For example, the hemostatic agent may remain in place postoperative procedure, either forming a composite with the hydrogel or acting as a hemostatic depot, allowing for elution of the hemostatic agent over a post-operative period of time, thereby providing an extended treatment profile. Although a portion of the crosslinked hydrogel will typically be removed with the tissue, the remaining crosslinked hydrogel biodisintegrates slowly over time, with the potential to remain in place throughout and beyond the healing phase.

As previously noted, the present disclosure provides compositions and co-compositions for injecting into a patient.

In use, the administered composition or administered co-compositions (e.g., hydrogels, solutions, etc.) may be delivered to a target site of a patient via a suitable medical device (e.g., a syringe or a fluid reservoir coupled to an injection needle).

The compositions and co-compositions may have a viscosity suitable for injection from a selected medical device. In some embodiments, the composition or co-compositions may be pseudoplastic. Pseudoplasticity generally refers to the property of decreasing in viscosity upon the application of shear force. Thus, for example, the composition may have a higher viscosity at rest or under low shear conditions (e.g., while stored in a container) than while under high shear conditions (e.g., during loading into and/or injection through a needle).

The compositions and co-compositions may be sterilized by various methods. For example, compositions and co-compositions may be autoclaved while inside a reservoir, such as a syringe barrel, by heating the mixture at or to a temperature of about 121° C. Alternatively or additionally, the compositions and co-compositions may be sterilized via sterile filtration and/or by gamma or electron beam irradiation introduction into the reservoir.

The present disclosure also provides medical devices comprising the compositions and co-compositions described herein. The medical devices may be used for injecting the composition or co-compositions to a tissue in a patient, e.g., for resecting at least a portion of the tissue.

According to some aspects of the present disclosure, the medical device may comprise one or more reservoirs. The reservoir(s) may serve as container(s) for the composition and co-compositions described herein. Suitable reservoirs may include, for example, syringe barrels (e.g., syringe barrels compatible with a manual or automatic injection system), flexible pouches such as plastic bags, and other fluid containers configured for use with a suitable injection needle. Exemplary materials suitable for the reservoir include, but are not limited to, cyclic olefin copolymer, cyclic olefin polymer, polypropylene, polycarbonate, polyvinyl chloride, and glass.

The medical device herein may comprise one or more needles. In some examples, the reservoir(s) of the medical device may be directly coupled to the needle(s), e.g., via a Luer adapter or other suitable connection, or may be indirectly coupled to the needle(s) via a flexible tube, such as a catheter. Non-limiting examples of needles coupled with a reservoir via a flexible tube include Interject™ sclerotherapy needles by Boston Scientific. In some examples, the needle(s) may be hypodermic needle(s), and may range from a size of 7 gauge (4.57 mm outer diameter (OD), 3.81 mm inner diameter (ID)) to 33 gauge (0.18 mm OD, 0.08 mm ID), e.g., having a size ranging from 16 gauge (1.65 mm OD, 1.19 mm ID) to 21 gauge (0.82 mm OD, 0.51 mm ID) to 22 gauge (0.72 mm OD, 0.41 mm ID) to 23 gauge (0.64 mm OD, 0.33 ID) to 24 gauge (0.57 mm OD, 0.31 mm ID), among other sizes. Exemplary materials for the needle(s) include, but are not limited to, metals and metal alloys, such as stainless steel and Nitinol, and polymers. The distal tip of the needle(s) may be sharpened, and may have a beveled shape. The proximal end of the needle(s) may include a suitable fitting/adaptor (e.g., a Luer adapter) for engagement with a syringe barrel or other reservoir. In some examples, the needle may include an elongated tube or catheter between the needle tip and the proximal fitting/adapter.

Further disclosed herein are methods of resecting at least a portion of a tissue from a subject (e.g., a human patient). The methods may comprise injecting the compositions described herein to a tissue of the subject and resecting at least a portion of the tissue from the patient.

FIG. 1A illustrates an exemplary syringe 10 providing a reservoir for a composition or co-composition 15 as discussed above. The syringe 10 may comprise a barrel 12, a plunger 14, and one or more stoppers 16. The barrel 12 may include a Luer adapter (or other suitable adapter/connector), e.g., at the distal end 18 of the barrel 12, for attachment to an injection needle 50 via a flexible catheter 29. The proximal end of the catheter 29 may include a suitable connection 20 for receiving the barrel 12. In other examples, the barrel 12 may be directly coupled to the injection needle 50. The syringe barrel 12 may serve as a reservoir, containing the composition or co-composition 15 for injection through the needle 50.

Figure 1B:
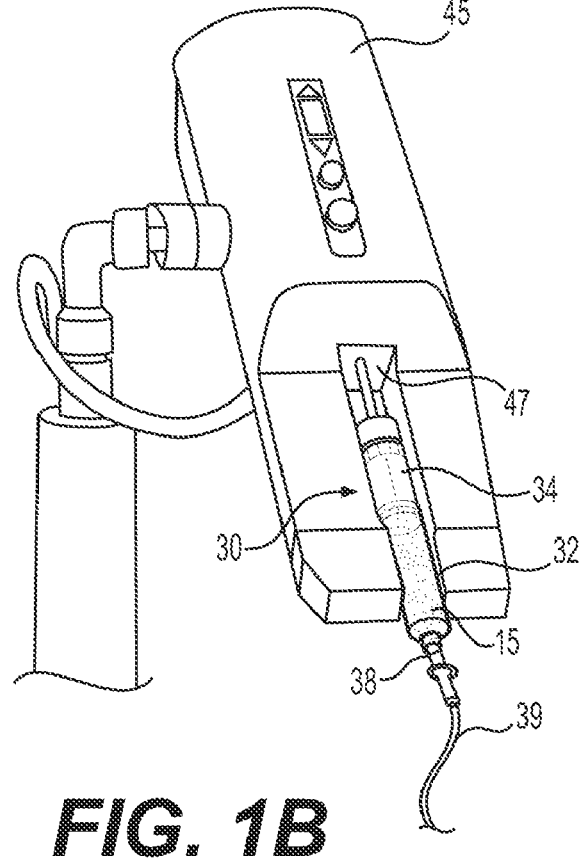

FIG. 1B illustrates an exemplary syringe 30 for use with an automatic injection system 45. The syringe 30 may include any of the features of the syringe 10 of FIG. 1A, e.g., a barrel 32, a plunger 34, and a Luer adapter (or another suitable adapter/connector) at the distal end 38 of the barrel 32. A composition or co-composition 15 as discussed above may be loaded in the barrel 32, and the syringe 30 may be inserted into a channel 47 of the injection system 45 for automatic control over the amount of hydrogel injected. The distal end 38 of the syringe 30 may be coupled to an injection needle (e.g., similar to injection needle 50 of FIG. 1A) via a catheter 39. According to some aspects of the present disclosure, the plunger 34 may form part of the injection system 45 and the barrel 32 may be a separate component, e.g., a replaceable cartridge, to be connected to the injection system 45. For example, the composition or co-composition 15 may be prepared in the barrel 32 as a replaceable cartridge having a proximal attachment compatible with a plunger component of the injection system 45.

Figure 1C:
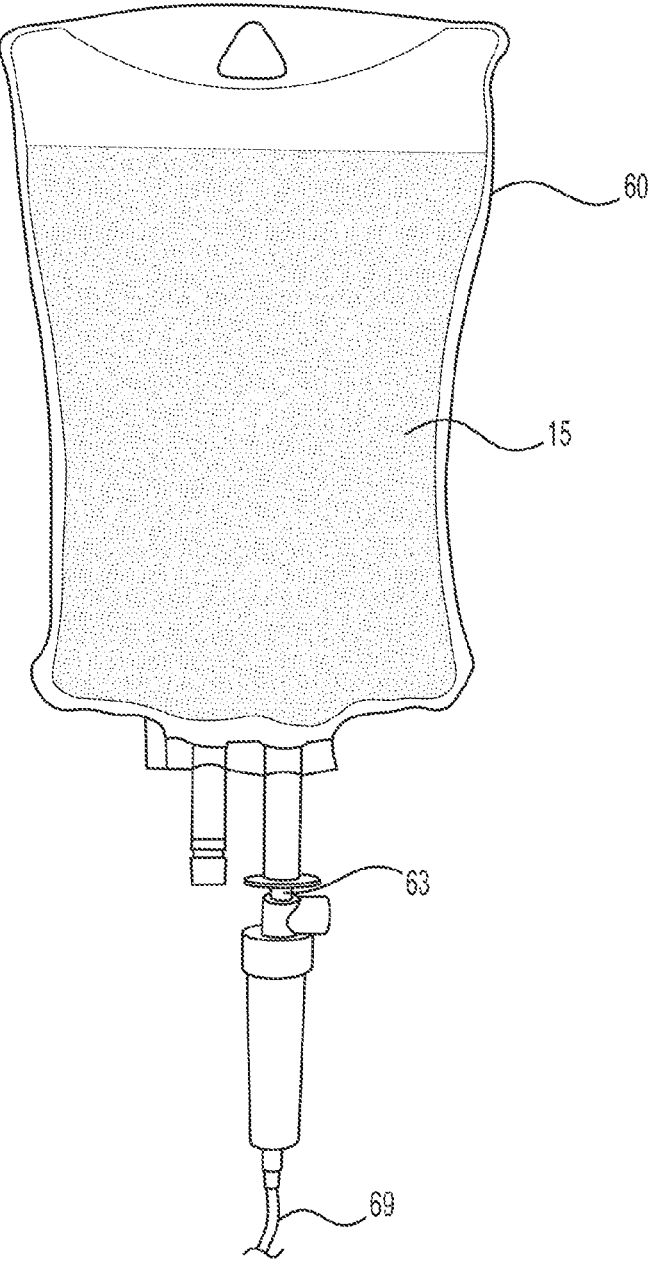

FIG. 1C illustrates an exemplary reservoir 60 according to some aspects of the present disclosure. The reservoir 60 may be provided by a flexible pouch or bag, such as an IV bag. A composition or co-composition 15 as described herein may be loaded in the reservoir 60. The reservoir 60 may be sterile, and may comprise a plastic material such as polyvinyl chloride (PVC) (e.g., with a plasticizer such as bis(2-ethylhexyl) phthalate (DEHP)) or a non-PVC plastic material. The pouch may include a Luer adapter 63 for attachment to a catheter 69 and/or needle (having any suitable gauge size, as described above) for injecting the composition or co-composition 15 into a patient. The reservoir 60 may be compressible, e.g., to allow for delivery of the composition through the catheter 69 and/or needle by compression of the reservoir 60.

The amount of force required to move the composition or co-composition through a needle aperture (generally described as "peak load" force) may depend on the viscosity of the composition or co-composition, the dimensions of the needle (inner diameter, outer diameter, and/or length), and/or the material(s) from which the needle is formed. For example, a greater amount of force may be applied to inject the composition or co-composition through a 33 gauge needle in comparison to a 7 gauge needle. Additional factors that may affect the amount of force applied to inject the composition or co-composition may include the dimensions of a catheter (inner diameter, outer diameter, and/or length)

connecting the reservoir to the needle. Suitable peak loads for injection with one or two hands may range from about 5 lbf to about 25 lbf, such as from about 10 lbf to about 20 lbf, e.g., about 15 lbf. The loads measured for a given hydrogel concentration may vary for different needles and flow rates. An injection system having a machine-drive plunger like that shown in FIG. 1B may also be useful for cases where higher peak load forces are required.

According to some aspects of the present disclosure, the size of the needle may be chosen based on the viscosity and/or components of the composition or co-composition, or vice versa. Further, the dimensions of the catheter tubing (inner diameter, outer diameter, and/or length), if any, may affect the types and amount of force applied to the composition or co-composition during injection. These parameters may be taken into consideration according to the properties of the composition or co-composition and the needs of the patient. According to some aspects of the present disclosure, the size of the needle may be 23 gauge or 25 gauge. In some cases, a larger size of 20 gauge, 21 gauge, or 22 gauge may be used to inject the composition or co-composition.

The composition or co-compositions described herein may be used in various medical procedures, including tissue resection and dissection procedures of the GI system, the respiratory system, and/or the genitourinary system. The tissue resected or dissected in such medical procedures may comprise diseased or injured tissue, non-diseased tissue, or a combination thereof. Exemplary tissue resection procedures include endoscopic mucosal resection (EMR) and endoscopic submucosal dissection (ESD) as noted above. In these procedures, an endoscope is typically inserted into the patient's esophagus and advanced through the GI system to reach a target site in the esophagus, stomach, or intestine. EMR is typically used for removal of tissue smaller than 2 cm in diameter, e.g., to biopsy tissue or to remove injured or diseased tissue (e.g., a cancerous lesion), while ESD is typically used for removal of larger lesions.

In some aspects, a composition or co-compositions as described herein may be injected between two layers of tissue, e.g., injected into submucosal tissue between an upper mucosal layer and lower muscularis propria layer at a target treatment site. The composition or co-compositions may be injected within the submucosal space (submucosal layer) under a portion of tissue, whereupon the injected material may cause the mucosal tissue to separate from the muscularis propria layer, elevating the mucosal tissue layer. A suitable cutting device, e.g., an electrocautery cutting device such as a knife, snare, scissors, or forceps, may then be used to remove the portion of tissue. For removal of larger portions of tissue (e.g., via ESD), the composition or co-compositions may be injected under the portion of tissue, wherein the hydrogel elevates the upper layer of tissue from the lower layer. The cutting device then may be used to make an incision around the portion of tissue and remove it. The composition or co-compositions may be injected in the submucosal layer to assist in removing additional portions of tissue.

In various aspects, hydrogel maintains separation of the tissue layers throughout the entire resection procedure. A portion of hydrogel may be removed via the resection process. However, at least a portion of the hydrogel will typically remain in place after the procedure in contact one or more of the tissue layers as discussed further below.

Figures 2A, 2B, 2C, 2D:
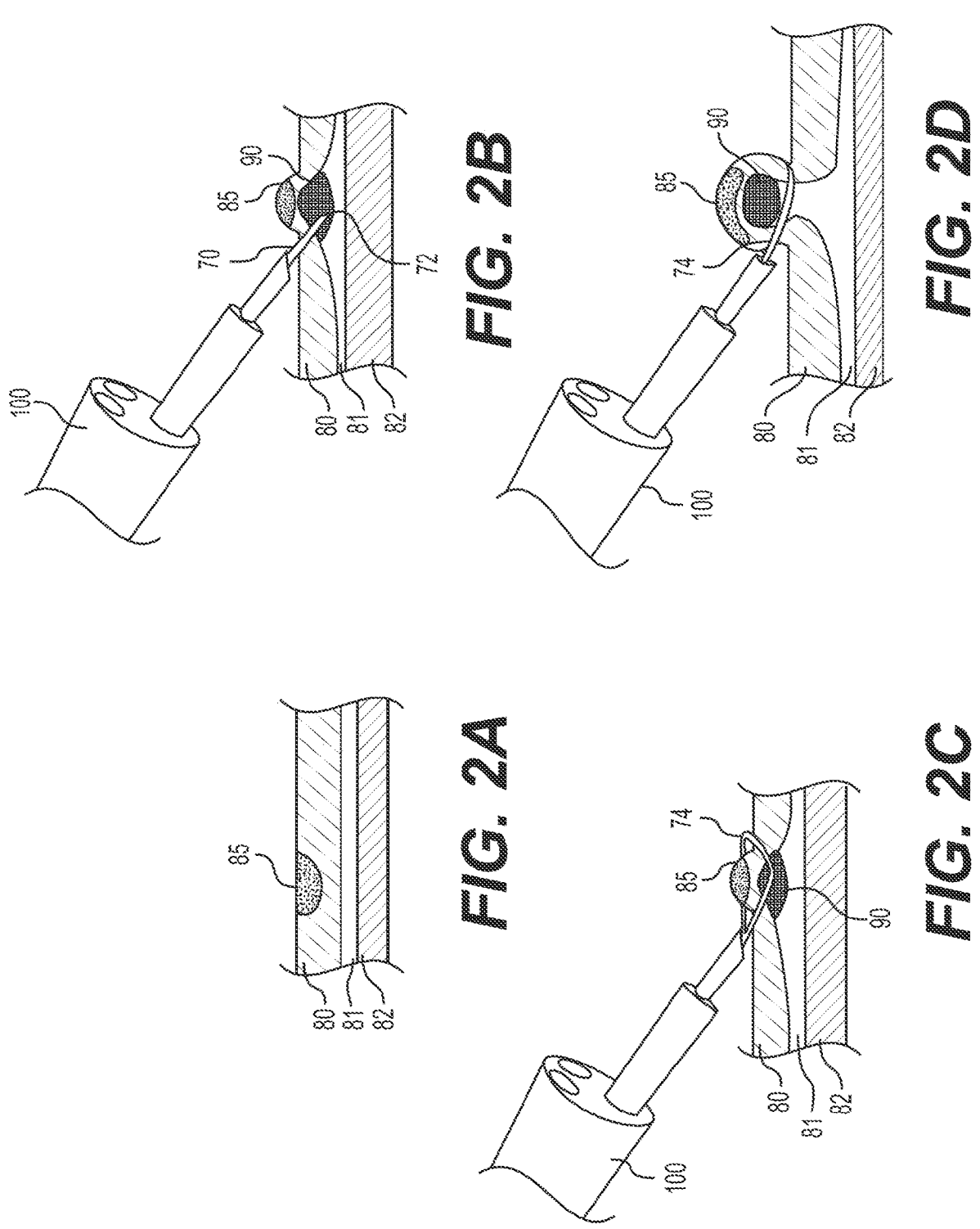
FIGS. 2A-2E illustrate an exemplary tissue resection procedure in accordance with certain aspects of the present disclosure.

FIGS. 2A-2E illustrate an exemplary resection procedure according to some aspects of the present disclosure. For example, the procedure may be EMR or ESD as discussed above, or any other suitable medical procedure for resecting tissue. FIG. 2A shows a cross-sectional view of two portions of tissue or tissue layers 80, 82, which may be separated by a middle layer 81 of tissue (such as, e.g., upper mucosal and lower muscularis propria layers separated by a middle submucosal tissue layer). One or both of the portions of tissue 80, 82 may include a section of tissue 85 targeted for removal. For example, the section of tissue 85 may comprise injured or diseased tissue, or may comprise tissue targeted for biopsy and subsequent analysis. In the example of FIG. 2A, the section of tissue 85 is located toward the tissue surface, however, the devices and compositions disclosed herein may be used to remove tissue from inner tissue layers.

As shown in FIG. 2B, an endoscope 100 defining one or more lumens (e.g., three lumens as shown) may be used to deliver a needle 70 to the treatment site. The needle 70 may have a hollow lumen and a sharp, beveled tip 72 for piercing the tissue surface such that the needle tip 72 is within the middle layer 81 between the upper and lower portions of tissue 80, 82. The needle lumen may be in communication with a fluid reservoir, such as a syringe or other reservoir containing a composition or co-compositions prepared as discussed above. The syringe may be used to inject the composition or co-compositions into the middle layer 81 between the portions of tissue 80, 82 to form a cushion or bleb of polysaccharide-based hydrogel 90, as shown in FIG. 2B. Once the composition or combined co-compositions is/are injected, the volume of the polysaccharide-based hydrogel 90 (also referred to hereinabove as the polysaccharide-based hydrogel at the point of administration) may cause the upper and lower portions of tissue 80, 82 to separate, such that the section of tissue 85 may be elevated from underlying tissue. An electrocautery snare 74 or other cutting device 74 (such as, e.g., an electrocautery knife, scissors, or forceps, among other suitable cutting devices) may be used to cut and remove the section of tissue 85, as shown in FIGS. 2C and 2D.

Figure 2E:
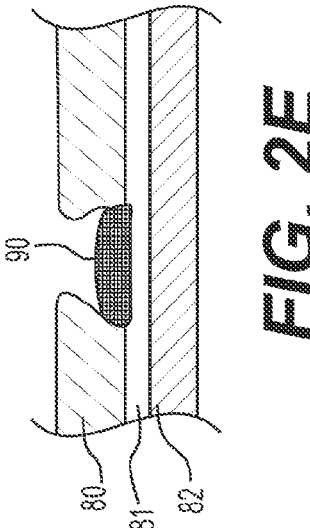

Once the section of tissue 85 is removed, as shown in FIG. 2E, a portion of the polysaccharide-based hydrogel 90 remains in place after the procedure in contact one or more of the tissue layers 80, 81, 82. In this way the polysaccharide-based hydrogel 90 can act as a barrier (i.e., as a "band-aid") to protect the wound and/or to reduce or prevent blood flow after tissue resection or dissection, until the polysaccharide-based hydrogel biodisintegrates. In some embodiments, the polysaccharide-based hydrogel 90 can also act as a depot for the hemostatic agent, allowing for elution of the hemostatic agent during the procedure and/or over a post-operative period of time, providing an immediate and/or extended treatment profile.

Example 1

Raw Materials:

Orise® is commercially available from Boston Scientific Corporation, Marlborough MA, USA. Gellan gum was provided as the low acyl CG-LA grade Kelcogel® from CP Kelco US Inc. Atlanta, GA, USA. Salts were prepared as calcium chloride and sodium chloride solutions in sterile water. ChitosanFD is freeze-dried chitosan, more specifically, electro-sprayed particles of chitosan (acetate salt) crosslinked with tripolyphosphate (e.g., sodium tripolyphosphate) and subsequently freeze dried, and can be prepared in accordance with Example 1 of U.S. Patent Pub. No. 2021/0322629.

Samples were milled and screened to <50 um. Hydroxyapatite nanopowder (<200 nm PSD, 97%) was provided by Aldrich (MilliporeSigma, St. Louis, MO, USA). Aminocaproic Add (ACA) (received as 6-aminohexanoic acid) was provided by Merck (Merck & Co. Inc., Branchburg, NJ), USA. Tranexamic acid (TXA) was provided by Merck as neat powder. Ninhydrin powder (spectrophotometric grade) was provided by Merck.

Pre-Formed Gel Preparation

Composite-Loaded Pre-formed Hydrogel: Commercially available Orise® (polysaccharide-based) hydrogel was loaded into a small mixing vessel and stirred at 300 rpm. Composite material (5% w/w chitosanFD (milled <50 um) or 10% w/w chitosanFD (milled <50 um) or 5% w/w hydroxyapatite (200 nm)) was added to the stirred hydrogel and mixed for <10 min at room temperature. Upon completion of mixing, the syringe (10 ml) was back-loaded before storing under refrigeration.

Drug-Loaded Pre-formed Hydrogel: Commercially available polysaccharide-based hydrogel was loaded into a small mixing vessel and stirred at 300 rpm. API drug powder (25% w/w aminocaproic acid or 15% w/w tranexamic acid) was added to the stirred hydrogel and mixed for <10 min at room temperature. Upon completion of mixing, the syringe (10 ml) was back-loaded before storing under refrigeration.

Pre-Loaded Gel Preparation

Composite-Loaded Formed Hydrogel (<1.5% GG w/w final Composition): Gellan Gum (polysaccharide) raw material was hydrated (2h, +70° C.), then cooled to 40° C. Once cooled, the composite material (5% w/w chitosanFD (milled <50 um) or 10% w/w chitosanFD (milled <50 um) or 5% w/w hydroxyapatite (200 nm)) was added with stirring followed by a solution of crosslinker salt (calcium chloride and sodium chloride). The mixture was stirred for an additional <10 minutes before loading into syringe (3 ml or 10 ml) and stored under refrigeration.

Attribute Testing

Injection Force Assessment: Gel-loaded syringes were tested using an Instron Tensile Tester 5965 (Instron, Norwood, MA, USA), with selected needle gauges (18 G or 19 G) or Interject™ dosing catheters (Boston Scientific). Injectability trials were conducted at 20 mm travel distance at 2.36 mm/s. A 100N force gauge was equipped and prototypes were benchmarked versus commercial Orise®.

TABLE 1

| Injection Force Assessment | |
| --- | --- |
| Composition | Max Inj. Force (Interject ™). Dosing Catheter) |
| Commercial Orise | 54N |
| w/ 10% ChitosanFD at <50 um PSD | Exceed 100N |
| w/ 5% ChitosanFD at <50 um PSD | Exceed 100N |
| w/ 5% Hydroxyapatite at <200 nm PSD | 58N |

Results demonstrated successful and comparative max injection force for the composition contain 5% hydroxyapatite at <200 nm. ChitosanFD at levels 5% and 10% exceeded the 100N limit of the apparatus. This observation concluded that the composite materials are preferably approximately 200 μm particle size.

Kinetic Drug Release: Drug-loaded prototypes (1 g) were loaded into 6-well transwell plates with 6 ml D-PBS (Dulbecco's phosphate-buffered saline) and agitated at 100 rpm (rotary incubator) at 37° C. 500 μl aliquots of supernatant were extracted at 0 hr, 2 hr, 4 hr, and 24 hr (Extracted supernatant was replenished with 500 μl DPBS). 20 μl of supernatant was added to 100 μl 2% w/w ninhydrin solution.

The combined solution was heated until a purple colour emerged (+70° C., >10 min). The solution was cooled to room temperature and 500 μl ethanol was added. A 100 ul aliquot of the final purple solution was transferred to a 96 well UV-transparent well plate and analysed at 570 nm on BioTek Epoch UV plate reader (Agilent Technologies, Santa Clara, CA, USA). Recovery results were determined versus a comparative drug calibration curve.

2% Ninhydrin Solution Preparation: 2% ninhydrin powder in 50:50 Ethanol:0.05% Glacial Acetic Acid.

Calibration curves were prepared at target concentration 60, 30, 15, 7.5 mg/ml drug (ACA or TXA) in D-PBS. 20 μl aliquot was added to 100 ul 2% Ninhydrin solution. The combined solution was heated until a purple colour emerged (+70° C., >10 min). The solution was cooled to room temperature and 500 ul ethanol added. A 100 ul aliquot of the final purple solution was transferred to a 96 UV-transparent well plate and analysed at 570 nm.

Figure 3:
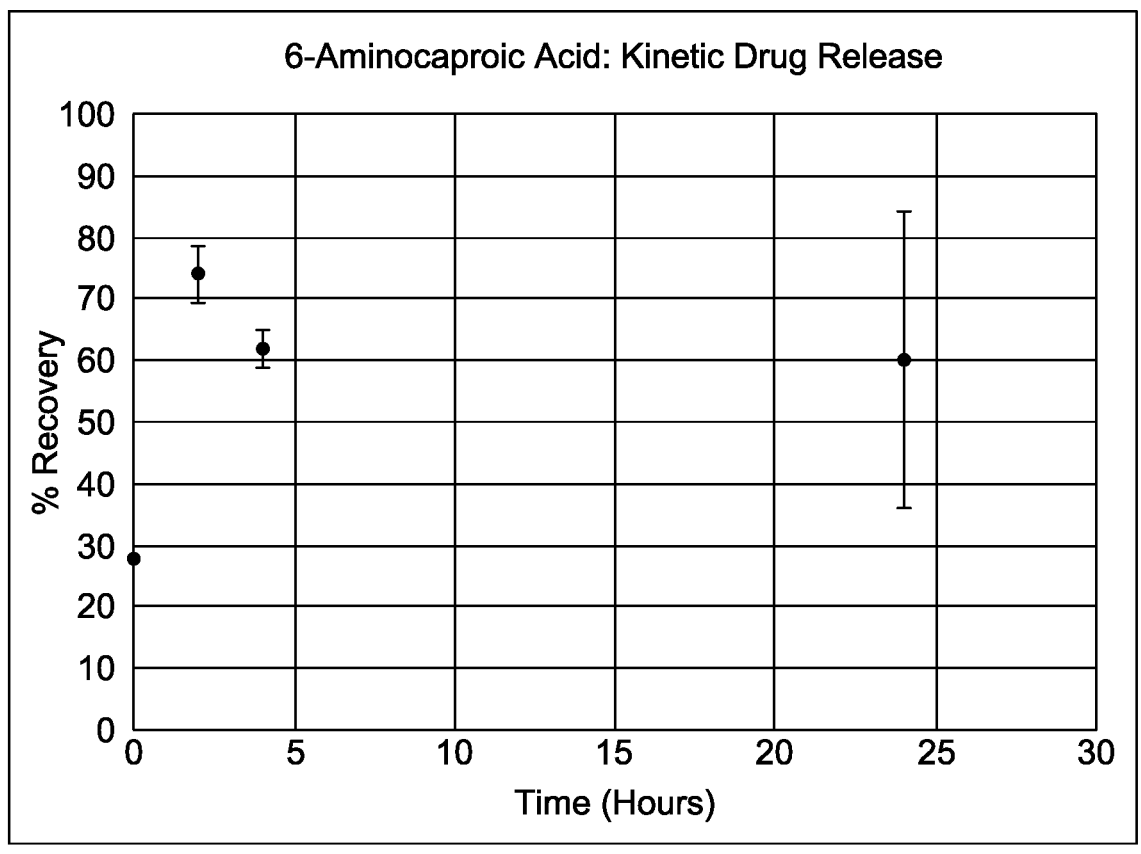
FIG. 3 illustrate recovery of 6-aminocaproic acid in D-PBS supernatant as a function of time in accordance with an aspect of the present disclosure.

Kinetic drug release analysis showed <80% mean recovery of 6-aminocaproic acid in the D-PBS supernatant within 2 hrs of dosing (see FIG. 3). This demonstrated appropriate gel loading with an amino-acid drug product, dosing as required, and immediate elution.

Figure 4:
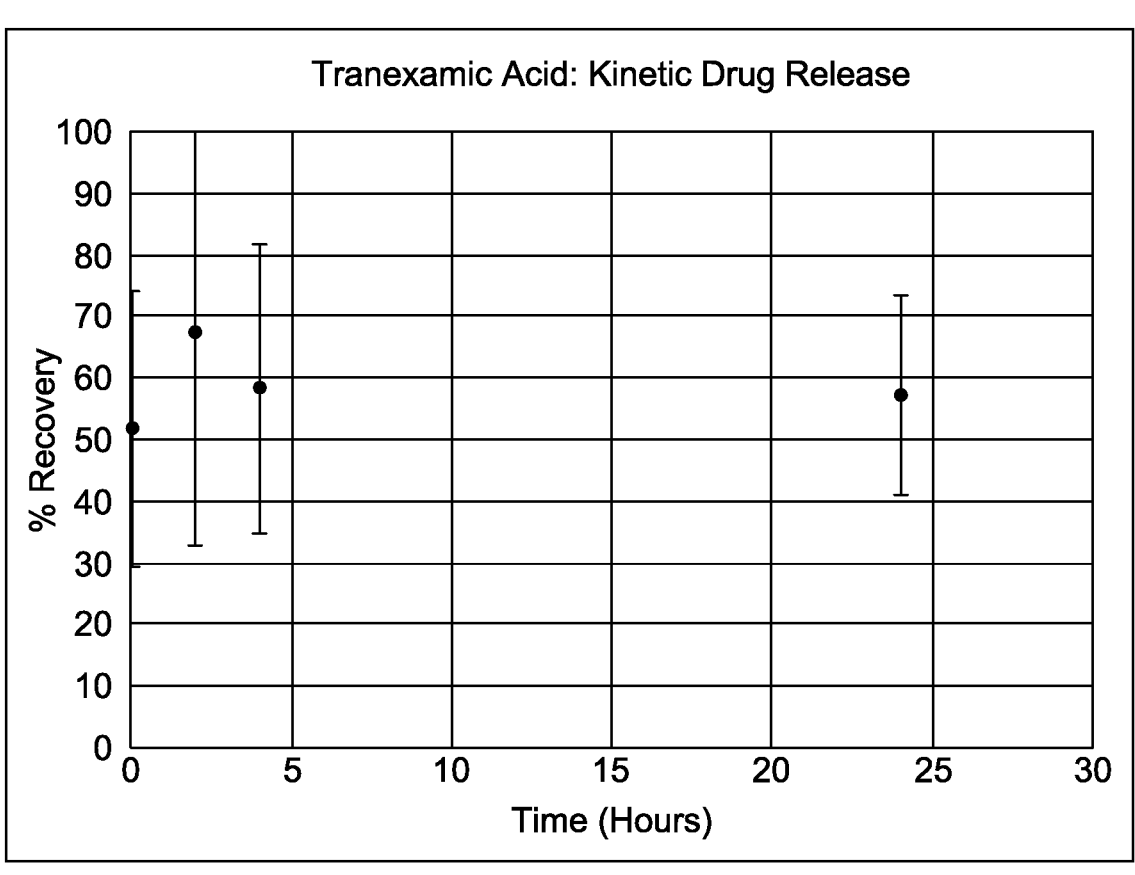
FIG. 4 illustrate recovery of tranexamic acid in D-PBS supernatant as a function of time in accordance with an aspect of the present disclosure.

Kinetic drug release analysis showed <70% mean recovery of tranexamic acid in the D-PBS supernatant within 2 hrs of dosing (see FIG. 4). This demonstrated appropriate gel loading with a further amino-acid drug product, dosing as required, and immediate elution.

Example 2

ChitosanFD (freeze-dried, electro-sprayed particles of chitosan acetate crosslinked with tripolyphosphate) of ~5000 nm average particle size is prepared by ball-milling in a P7 Planetary Mill (e.g., Fritsch PULVERISETTE Planetary Ball Mill, FRITSCH Milling and Sizing, Inc., Pittsboro, NC, USA), 80 mg ChitosanFD, zirconium microbeads (1.4 mm, 20 g) In hexane at 400 rpm, 10 min).

Figure 5:
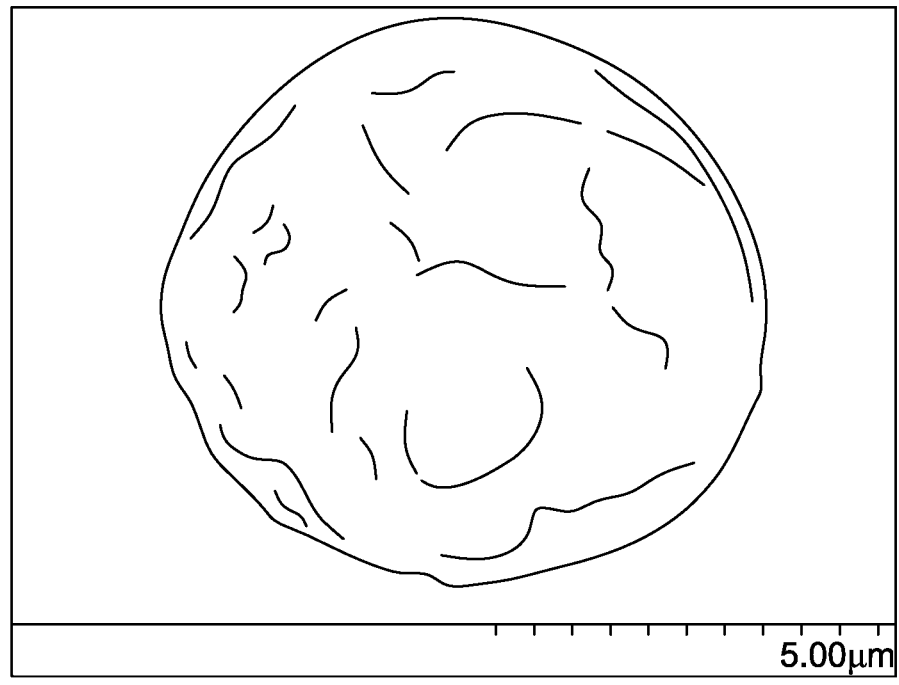
FIG. 5 is a micrograph of a particulate hemostatic agent having a core comprising a chitosan salt and a shell comprising tripolyphosphate.
Figure 6:
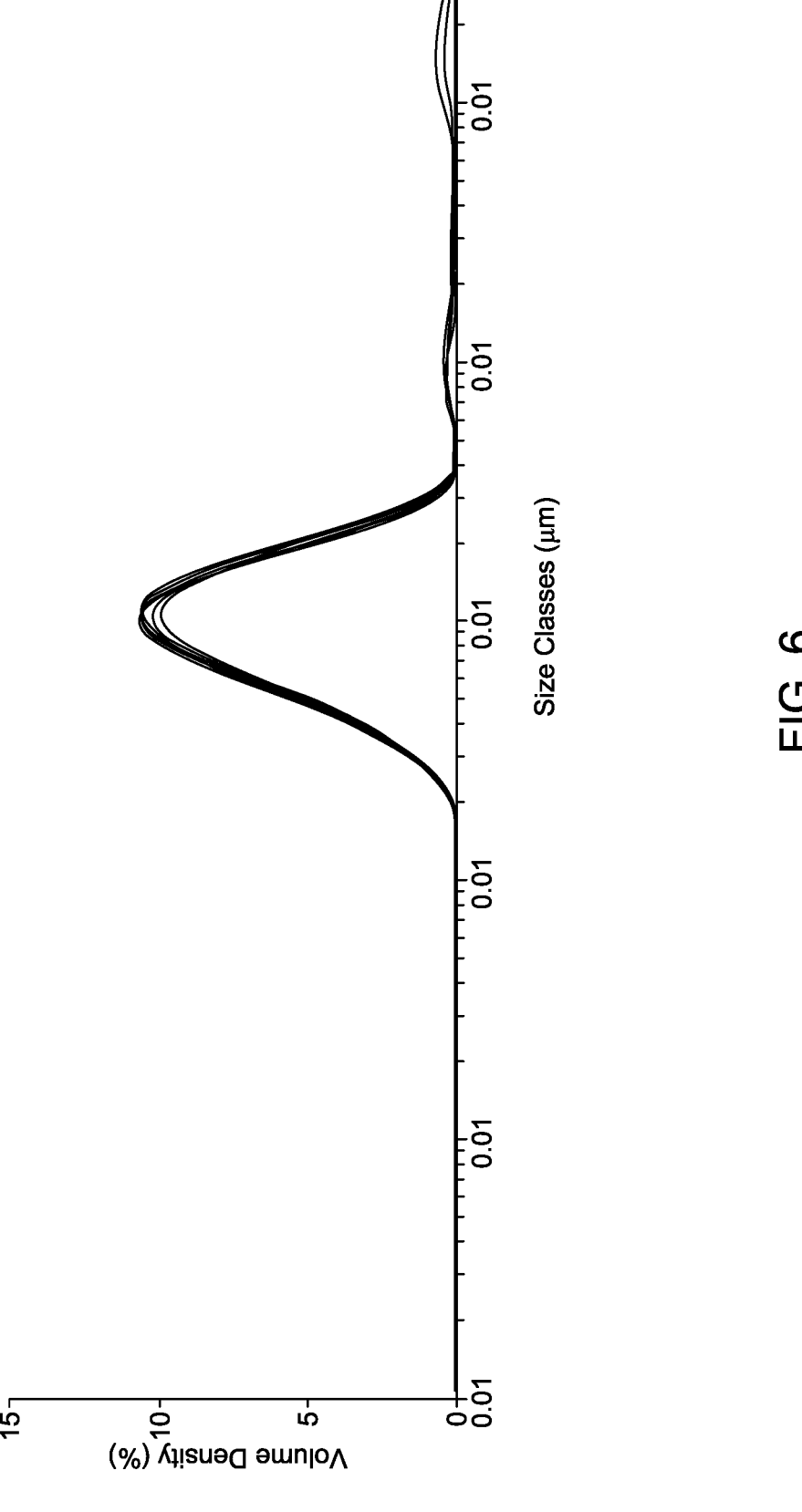
FIG. 6 is a graph of particle size distribution, volume density (%) vs. particle size (μm), for a collection of hemostatic agent particles having a core comprising a chitosan salt and a shell comprising tripolyphosphate.

Spray dried particles having a chitosan core coated with tripolyphosphate were produced. Chitosan particles were prepared as follows: chitosan solution (ultrahigh molecular weight chitosan dissolved in aqueous acetic acid solution) and aqueous tripolyphosphate solution were spray-dried in a Buchi B-290 Mini Spray Drier with a Three Fluid Nozzle (BUCHI Corporation, New Castle, DE, USA). Aqueous chitosan-acetate was fed to the inner fluid nozzle and aqueous tripolyphosphate solution was fed to the outer fluid nozzle, creating a core/shell structure having a chitosan core and a tripolyphosphate shell (where chitosan is crosslinked by tripolyphosphate to the extent that they intermingle at the interface). Outlet temperature is set at a relatively low 49° C. to reduce risk of degradation. FIG. 5 is a micrograph of a core/shell particle produced by this process. FIG. 6 is a graph showing particle size distributions, volume density (%) vs. particle size (μm), as measured by Malvern Mastersizer (Malvern Instruments, Malvern, UK), for particle collections produced according to the above procedure.

Commercially available Orise® hydrogel was loaded into a small mixing vessel and stirred at 300 rpm. 5% w/w chitosanFD was added to the stirred hydrogel and mixed for <10 min at room temperature. Upon completion of mixing, the syringe (10 ml) was back-loaded before storing under refrigeration.

Gel-loaded syringes were tested using an Instron Tensile Tester 5965 and 23 G Interject™ dosing catheter as described above. Prototypes were benchmarked versus commercial Orise®.

TABLE 2

| Injection Force Assessment | |
| --- | --- |
| Composition | Max Inj. Force (Interject $^{TM}_{xx}$ Dosing Catheter) |
| Core/shell chitosan/tripolyphosphate | 50N |
| Commercial Orise ® | 47N |

The invention claimed is:

1. An injectable polysaccharide-based hydrogel that comprises an anionic polysaccharide, a cationic crosslinking agent and a hemostatic agent.

2. The injectable polysaccharide-based hydrogel of claim 1, wherein the anionic polysaccharide is provided at a concentration ranging from about 0.05% to about 1.0%, with respect to the total weight of the injectable polysaccharide-based hydrogel.

3. The injectable polysaccharide-based hydrogel of claim 1, wherein the hemostatic agent is selected from an organic polymeric hemostatic agent, a small molecule organic hemostatic agent, a large molecule organic hemostatic agent, and an inorganic hemostatic agent.

4. The injectable polysaccharide-based hydrogel of claim 3, wherein the hemostatic agent is selected from chitosan, hydroxyapatite or tranexamic acid.

5. The injectable polysaccharide-based hydrogel of claim 1, wherein the hemostatic agent is in particulate form and is less than 50000 nm in average particle size.

6. The injectable polysaccharide-based hydrogel of claim 5, wherein the hemostatic agent comprises a core comprising a chitosan salt and a shell comprising a polyanionic crosslinking agent.

7. The injectable polysaccharide-based hydrogel of claim 1, wherein the hemostatic agent is provided at a concentration ranging from about 5% to about 50%, with respect to the total weight of the injectable polysaccharide-based hydrogel.

8. A method of separating and elevating an upper mucosal layer from a lower layer, the method comprising injecting the injectable polysaccharide-based hydrogel of claim 1 through a needle into a target treatment site between the upper mucosal layer and the lower layer.

9. The method of claim 8, wherein the method is performed as part of an endoscopic mucosal resection procedure or an endoscopic submucosal dissection procedure.

10. The method of claim 8, wherein the medical device further comprises a flexible tube that couples the syringe barrel to the needle and wherein the injectable polysaccharide-based hydrogel is injected from the syringe barrel, through the flexible tube, through the needle and into the target site.

11. The injectable polysaccharide-based hydrogel of claim 1, wherein the anionic polysaccharide contains a repeating unit of glucuronic acid.

12. The injectable polysaccharide-based hydrogel of claim 1, wherein the anionic polysaccharide comprises gellan gum.

13. The injectable polysaccharide-based hydrogel of claim 1, wherein the cationic crosslinking agent comprises a salt comprising a divalent metal cation.

14. The injectable polysaccharide-based hydrogel of claim 1, wherein the cationic crosslinking agent is provided at a concentration ranging from about 0.01%% to about 0.25%, with respect to the total weight of the injectable polysaccharide-based hydrogel.

15. A medical device comprising a reservoir that contains the injectable polysaccharide-based hydrogel of claim 1.

16. The medical device of claim 15, wherein the reservoir is a syringe barrel.

17. The medical device of claim 16, wherein the medical device further comprises a needle through which the injectable polysaccharide-based hydrogel is injected.

18. Use of the medical device of claim 17 in a medical procedure in which an upper mucosal layer is elevated from a lower layer.

19. A kit comprising the medical device of claim 17 and one or more items selected from (a) an endoscopic injection needle, (b) tissue resection device, (c) a tissue retrieval device, and (d) an endoscope, within a suitable packaging material.

20. The method of claim 8, comprising removing tissue raised by the injectable polysaccharide-based hydrogel.

* * * * *